US007245977B1

(12) United States Patent
Simkins

(10) Patent No.: US 7,245,977 B1
(45) Date of Patent: Jul. 17, 2007

(54) SYSTEMS AND METHODS FOR MASS CUSTOMIZATION

(75) Inventor: Barry A. Simkins, Los Gatos, CA (US)

(73) Assignee: Align Technology, Inc., Santa Clara, CA (US)

( * ) Notice: Subject to any disclaimer, the term of this patent is extended or adjusted under 35 U.S.C. 154(b) by 802 days.

(21) Appl. No.: 09/620,253

(22) Filed: Jul. 20, 2000

(51) Int. Cl.
G06F 19/00 (2006.01)
(52) U.S. Cl. .................... 700/98; 700/161; 433/172
(58) Field of Classification Search ................ 700/161, 700/162, 98, 118, 182, 188, 173, 190, 68, 700/97, 163, 180, 184, 120, 119; 433/172, 433/2, 24, 212, 213, 20.1, 219; 600/300; 703/11; 164/34, 41; 246/16–17
See application file for complete search history.

(56) References Cited

U.S. PATENT DOCUMENTS

| | | | |
|---|---|---|---|
| 2,467,432 A | 4/1949 | Kesling | |
| 3,407,500 A | 10/1968 | Kesling | |
| 3,600,808 A | 8/1971 | Reeve | |
| 3,660,900 A | 5/1972 | Andrews | |
| 3,683,502 A | 8/1972 | Wallshein | |
| 3,738,005 A | 6/1973 | Cohen | |
| 3,860,803 A | 1/1975 | Levine | |
| 3,916,526 A | 11/1975 | Schudy | |
| 3,922,786 A | 12/1975 | Lavin | |
| 3,950,851 A | 4/1976 | Bergersen | |
| 3,983,628 A | 10/1976 | Acevedo | |
| 4,014,096 A | 3/1977 | Dellinger | |
| 4,195,046 A | 3/1980 | Kesling | |
| 4,253,828 A | 3/1981 | Coles et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,478,580 A | 10/1984 | Barrut | |
| 4,500,294 A | 2/1985 | Lewis | |
| 4,504,225 A | 3/1985 | Yoshii | |
| 4,505,673 A | 3/1985 | Yoshii | |
| 4,526,540 A | 7/1985 | Dellinger | |
| 4,575,330 A | 3/1986 | Hull | |
| 4,575,805 A * | 3/1986 | Moermann et al. | ......... 700/163 |
| 4,591,341 A | 5/1986 | Andrews | |
| 4,609,349 A | 9/1986 | Cain | |
| 4,611,288 A | 9/1986 | Duret et al. | |
| 4,656,860 A | 4/1987 | Orthuber et al. | |

(Continued)

FOREIGN PATENT DOCUMENTS

AU 3031677 5/1979

(Continued)

OTHER PUBLICATIONS

Andrews, "The Six Keys to Optimal Occlusion", *Straight Wire*, Chapter 3 pp. 13-24.

(Continued)

*Primary Examiner*—Kidest Bahta
(74) *Attorney, Agent, or Firm*—Townsend and Townsend and Crew LLP

(57) ABSTRACT

A method facilitates mass customization of an object by generating a template representing data common to the object; generating specific data to customize the object in conjunction with the template; and fabricating a customized version of the object.

25 Claims, 8 Drawing Sheets

U.S. PATENT DOCUMENTS

| | | | |
|---|---|---|---|
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,367,478 A | 11/1994 | Hattori |
| 5,368,478 A | 11/1994 | Andreiko et al. |
| 5,382,164 A | 1/1995 | Stern |
| 5,395,238 A | 3/1995 | Andreiko et al. |
| 5,431,562 A * | 7/1995 | Andreiko et al. ............. 433/24 |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Anderson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,718,585 A * | 2/1998 | Dehoff et al. ............. 433/202.1 |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,803,788 A * | 9/1998 | Penberthy et al. .......... 446/391 |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chisti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,210,162 B1 * | 4/2001 | Chishti et al. ............. 433/213 |
| 6,217,325 B1 | 4/2001 | Chishti |
| 6,217,334 B1 | 4/2001 | Hultgren |
| 6,241,355 B1 * | 6/2001 | Barsky ................. 351/177 |
| 6,244,861 B1 | 6/2001 | Andreiko et al. |
| 6,244,926 B1 * | 6/2001 | George et al. ............. 446/391 |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,464,496 B1 * | 10/2002 | Sachdeva et al. ............. 433/24 |
| 6,482,298 B1 | 11/2002 | Bhatnagar |
| 6,524,101 B1 | 2/2003 | Phan et al. |
| 6,554,611 B2 | 4/2003 | Chishti et al. |
| 6,554,613 B1 * | 4/2003 | Sachdeva et al. ............. 433/24 |
| 6,572,372 B1 | 6/2003 | Phan et al. |
| 6,633,789 B1 * | 10/2003 | Nikolskiy et al. ............. 700/98 |
| 2003/0051255 A1 * | 3/2003 | Bulman et al. ............. 725/135 |
| 2004/0073417 A1 * | 4/2004 | Rubbert et al. ............. 703/11 |
| 2004/0265770 A1 * | 12/2004 | Chapoulaud et al. ......... 433/24 |

FOREIGN PATENT DOCUMENTS

| | | |
|---|---|---|
| AU | 517102 | 7/1981 |
| AU | 5598894 | 6/1994 |
| CA | 1121955 | 4/1982 |
| DE | 2749802 | 5/1978 |
| DE | 69327661 | 7/2000 |
| EP | 091876 A1 | 10/1983 |
| EP | 299490 A2 | 1/1989 |
| EP | 376873 A2 | 7/1990 |
| EP | 490848 B1 | 6/1992 |

| | | |
|---|---|---|
| EP | 0 667 753 | 8/1995 |
| EP | 774933 B1 | 5/1997 |
| EP | 541500 A1 | 6/1998 |
| EP | 731673 B1 | 9/1998 |
| ES | 463897 | 1/1980 |
| FR | 2369828 | 6/1978 |
| FR | 2369828 A1 | 6/1978 |
| FR | 2652256 A1 | 3/1991 |
| GB | 1550777 | 8/1979 |
| JP | 53-058191 | 5/1978 |
| JP | 04-28359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 | 5/1994 |
| WO | WO 94/10935 A1 | 5/1994 |
| WO | WO 98/32394 | 7/1998 |
| WO | WO 98/58596 | 7/1998 |
| WO | WO 98/44865 A1 | 10/1998 |
| WO | WO 98/58596 A1 | 12/1998 |

OTHER PUBLICATIONS

Biostar Opeation & Training Manual. Great Lakes Orthodontics, Ltd. 199 Fire Tower Drive, Tonawanda, New York. 14150-5890. 20 pages total.

Chiappone, "Constructing the gnathologic setup and positioner" *J. Clin. Orthod.* (1980) 14:121-133.

Cottingham, "Gnathologic clear plastic positioner" *Am. J. Orthod.* (1969) 55:23-31.

Cureton, "Correcting malaligned mandibular incisors with removable retainers" *J. Clin. Orthod.* (1996) 30:390-395.

Dent-X posted at http://www.dent-x.com/DentSim.htm Sep. 24, 1998, 6 pages ttoal.

Elsasser, "Some observations on the history and uses of the Kesling positioner" *Am. J. Orthod.* (1950) 36:368-374.

Kamada et al., "Case reports on tooth positioners using LTV vinyl silicone rubber" *J. Nihon University School of Dentistry* (1984) 26(1):11-29.

Kamada et al., "Construction of tooth positioners with LTV vinyl silicone rubber and some case reports" *J. Nihon University School of Dentistry* (1982) 24(1):1-27.

Kesling, "Coordinating the predetermined pattern and tooth positioner with conventional treatment" *Am. J. Orthod. Oral. Surg.* (1946) 32:285-293.

Kesling, "The philosophy of the tooth positioning appliance" *Am. J. Orthod. Oral. Surg.* (1945) 31(6):297-304.

Kleemann et al., "The speed positioner" *J. Clin. Orthod.* (1996) 30:673-680.

Kunii et al., "Articulation Simulation for an Intellignet Dental Care System" *Displays* (1994) 15:181-188.

Kuroda et al., "Three-dimensional dental cast analyzing system using laser scanning" *Am. J. Orthod. Dentofac. Orthop.* (1996) 110:365-369.

Nahoum et al., "The vacuum formed dental contour appliance" *The New York State Dental Journal* (1964) 30(9):385-390.

*Nippon Dental Review* "New orthodontic device dynamic positioner (D.P.)-I. Approach to the proposal of D.P. and transparent silicone rubber" (1980) 452:61-74.

*Nippon Dental Review* "New orthodontic device-dynamic positioner (D.P.)-II. Practical application and construction of D.P." (1980) 454:107-130.

*Nippon Dental Review* "New orthodontic device-dynamic positioner (D.P.)-III. Case reports of reversed occlusion" 1980) 457:146-164.

*Nippon Dental Review* "New orthodontic device-dynamic positioner (D.P.)-Case reports of reversed occlusion" (1980) 458:112-129.

Nishiyama et al., "A new construction of tooth repositioner by LTV vinyl silicone rubber" *J. Nihon University School of Dentistry* (1977) 19(2):93-102.

Cardinal Industrial Finishes, Powder Coatings information posted at http://www.cardinalpaint.com on Aug. 25, 2000, 2 pages total.

Proffit et al, "Contemporary Orthodontics" Second Edition, Chapter 15, pp. 470-533.

*Raintree Essix™ & ARS Materials, Inc.*, Raintree Essix™ Technical Magazine Table of Contents and Essix™ Applications, http://www.essix.com/magazine/default.html (Aug. 13, 1997) 7 pages total.

Richmond et al., "The development of the PAR Index (Peer Assessment Rating): reliability and validity" *European Journal of Orthodontics* (1992) 14:125-139.

Schroeder et al., Eds. *The Visual Toolkit*, Prentice Hall PTR, New Jersey (1998) Chapters 6, 8, and 9 (pp. 153-210, 309-354, and 355-428, respectively).

Shilliday, "Minimizing finishing problems with the mini-positioner" *Am. J. Orthod.* (1971) 59:596-599.

Warunek et al., "Clinical use of silicone elastomer applicances" *JCO* (1989) XXIII(10):694-700.

Warunek et al., "Physical and mechanical properties of elastomers in orthodontic positioners" *Am. J. Orthod. Dentofac. Orthop.* (1989) 95:388-400.

Wells, "Application of the positioner appliance in orthodontic treatment" *Am. J. Orthodont.* (1970) 58:351-366.

Alexander et al., "The DigiGraph Work Station Part 2, Clinical Management," *JCO* (Jul. 1990), pp. 402-407.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler et al., "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D for Comparative 3-D Serial Growth Pattern Studies of Oral-Facial Structures," Program and Abstracts of Papers, Feb. 1975, *Journal of Dental Research*, vol. 54, IADR Abstracts 1979, 2 pages total.

Altschuler, "3D Mapping of Maxillo-Facial Prosthesis," AADR Abstract #607, 1980, 2 pages total.

American Association for Dental Research, Summary of Activities, Mar. 20-23, 1980, Los Angeles, CA, p. 195.

Andersson et al., "Clinical Rsults with Titanium Crowns Fabricated with Machine Duplication and Spark Erosion," *Acta Odontological Scandinavia*, vol. 47 (1989), pp. 279-286.

Baumrind et al., "A stereophotogrammetric system for the detection of prosthesis loosening in total hip arthroplasty, Applications of Human Biostereometrics (NATO)," Proceedings of the Society of Photo-Optical Instrumentation Engineers, vol. 166, Jul. 9-13, 1978, pp. 112-123.

Baumrind et al., Mapping the Skull in 3-D, Reprinted from The Journal, *California Dental Association*, vol. 48, No. 2 (1972 Fall Issue) 11 pages total.

Baumrind et al., "Seminars in Orthodontics," *Seminars in Orthodontics*, vol. 7, No. 4 (Dec. 2001), p. 222.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. 1-25.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized diagnosis in Orthodontics for Epidemiological Studies" (progress report), Abstracts of Papers, *Journal of Dental Research*; vol. 71, Special Issue Mar. 1-14, 1992, pp. 28-36.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized analysis of occlusion in the postcanine dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Brandestini et al., "Computer Machined Ceramic Inlays: In Vitro Marginal Adaptation," *Journal of Dental Research*, vol. 64/Special Issue/Abstracts, IADR/AADR Abstracts 1985, 1 page total.

Brook et al., An Image Analysis System for the Determination of Tooth Dimensions from Study Casts: Comparison with Manual Measurements of Mesio-distal Diameter, Abstract of Papers, 1985, Dept. of Children's Dentistry and Orthodontics, *J Dent Res.*, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7, Jul. 1979; (Part 2) vol. 8, No. 8 pp. 539-551, Aug. 1979.

Burstone et al., "Precision adjustment of the transpalatal lingual arch: Computer arch form predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the gnathologic setup and positioner" *J. Clin. Orthod.*, 14:121-133, 1980.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, *Canadian Dental Journal*, vol. 54(9), , (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 3 pages total.

DenTrac Corporation, Dentrac document, pp. 4-13.

Duret et al., "CAD-CAM in Dentistry," *Journal of the American Dental Association*, vol. 117 (Nov. 1988), pp. 715-720.

Duret et al., "CAD/CAM imaging in dentistry," *Current Opinion in Dentistry*, vol. 1 (1991), pp. 150-154.

Duret, "The Dental CAD/CAM, General Description of the Project," *Hennson International Product Brochure*, Jan. 1986., 18 pages total.

Duret, "Vers une prosthese informatisee," (English translation also attached), *Tonus*, vol. 75, (Nov. 15, 1985), pp. 55-57.

Economides, "The Microcomputer in the Orthodontic Office," *JCO*, (Nov. 1979), pp. 767-772.

Elsasser, "Some observation on the history and uses of the Kesling positioner" *Am. J. Orthod.*, 36:368-374, 1950.

Faber et al.,"Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery," Abstract of Papers, *Journal of Dental Research*, vol. 70 (1987), pp. 754-760.

Gim-Alldent Deutschland, "Das DUX System: Die Technik".4 pages total.

Grayson, "New Methods for Three Dimensional Analysis of Craniofacial Deformity," Symposium: Computerized Facial Imaging in Oral and Maxilofacial Surgery, AAOMS Sep. 13, 1990, 3 pages total.

Guess et al., "Computer Treatment Estimates in Orthodontics and Orthognathic Surgery," *JCO*, (Apr. 1989), pp. 262-28.

Heaven et al., "Computer-based Image Analysis of Artificial Root Surface Caries," "Automated Identification of Landmarks in Cephalometric Radiographs," Abstracts of Papers, *Journal of Dental Research*, vol. 67, Mar. 9-13, 1988, 2 pages total.

Hoffmann et al., "Role Cephalometry for Planning of Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

Inside the ADA, *Journal Of The American Dental Assoc.*, vol. 118 (Mar. 1989) 9 pages total.

JCO Interviews, "Craig Andreiko, DDS, MS on the Elan and Orthos Systems", JCO, (Aug. 1994), pp. 459-468.

JCO Interviews, "Dr. Homer W. Phillips on Computers in Orthodontic Practice Part 2," JCO, (Dec. 1983), pp. 819-831.

Jerrold, "The problem, electronic data transmission and the law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case reports on tooth positioners using LTV vinyl silicone rubber" J. Nihon University School of Dentistry, 26(1):11-29, 1984.

Kanazawa et al., "Three-Dimensional Measurements of the Occlusal Surfaces of Upper Molars in a Dutch Population," *J. Dent Res.*, vol. 63, No. 11 (Nov. 1984), pp. 1298-1301.

Kesling, "The philosophy of the tooth positioning appliance" *Am. J. Orthod. Oral Surg.*, 31(6):297-304, 1945.

Kleemann et al., "The speed positioner", *J. Clin. Orthod.*, 30:673-680, 1996.

Laurendeau et al., "A Computer-Vision Technique for Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

McNamara et al., *Orthodontic and Orthopedic Treatment in the Mixed Dentition*, Needham Press, Jan. 1993. pp. 347-353.

McNamara et al., "Invisible Retainers", *J. Clinical Orthodontics*, (Aug. 1985) pp. 570-578.

Moermann et al., "Computer Machined Adhesive Porcelain Inlays: Margin Adaptation after Fatigue Stress," IADR Abstract 339, *Journal of Dental Research*, vol. 66(a) (1987), p. 339.

Mörmann et al., "Marginal Adaption von adhasiven Porzellaninlays in vitro," *Schwizerische Monatsshrift fur Zahnmedizin*, vol. 785 (1985), p. 1118-1129.

Mörmann et al., "Marginale Adaption von adhäsuven Porzellaninlays in vitro," Separatdruck aus: Schweiz. Mschr. Zahnmed. 95: 1118, 1985.

Nahoum, "The vacuum formed dental contour appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Pinkham, "'Foolish ' Concept Propels Technology," *Dentist*, Jan./Feb. 1989, 3 pages total.

Pinkham, "Inventor's CAD/CAM may transform dentistry," *Dentist*, Sep. 1990, 3 pages total.

Ponitz, Invisibte Retainers, 59 *Am. J. Orthodontics*, Mar. 1971, pp. 266-272.

Procera Research Projects, *PROCERA Research Projects 1993*—Abstract Collection, 1993, pp. 3-28.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, Feasibility of an Automated System for Production of "Dental Restorations," PhD Thesis, Univ. of Minnesota, Nov. 1988, 244 pages total.

Richmond et al., Research Reports, "The development of a 3D Cast Analysis System," *British Journal of Orthodontics*, pp. 53-54.

Richmond,"Recording the dental cast in three dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodintics: An approach with use of a computer network system," *Am. J. Orthod. Dentofac. Orthop.* vol. 101 No. 3 (Mar. 1992), pp. 210-220.

Schellhas et al., "Three-Dimensional Computer Tomography in Maxillofacial Surgical Planning," *Arch Otolamgol Head Neck Surg.* vol. 114 (Apr. 1988), pp. 438-442.

Segu et al., "Computer-aided Cefalometry and New Mechanics in Orthodontics" (Article Summary in English, article in German), *Fortschr, Kieferorthop*, 44, 370-376 (Nr. 5), 1983.

Siemens, CEREC—Computer-Reconstruction, High Tech in der Zahnmedizin, 14 pages total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, articel in German), *Dtsch Zahnärztl Z* 45, 314-322, 1990.

U.S. Department of Commerce, National Technical Information Service, "Automated Crown Replication Using Solid Photography SM, " Solid Photography Inc. Melville NY, Oct. 1977, 21 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed on Jun. 20, 1997, 41 pages total.

Van der Linden et al., "Three-Dimensional Analysis of Dental Casts by Means of the Optocom,"60 *J Dent Res*, Jul.-Aug. 1972, p. 1101.

Van der Linden, "A New Method to Determine Tooth Positions and Dental Arch Dimensions," Jul.-Aug. 1972, p. 1104.

Van der Zel, "Ceramic-fused-to-metal Restorations with a New CAD/CAM System," *Quintessense International*, vol. 24(11) (1993), pp. 769-778.

Várady et al., "Reverse Engineering of Geometiric Models—An Introduction," May 13, 1996, pp. 1-28.

Warunek et al., "Clinical use of silicone elastomer appliances" *JCO* , MH (10):694-700, 1989.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, New Advances in Personal Computer Applications for Cephalometric Analysis, Growth Prediction, Surgical Treatment Planning and Imaging Processing, Symposium: Computerized Facial Imaging in Oral and Maxilofacial Surgery, AAOMS, Sep. 13, 1990, p. 5.

Yamamoto et al., "Three-Dimensional Measurement of Dental Cast Profiles and Its Applications to Orthodontics, " Annual Int'l Conf. of IEEE Engineering in Medicine and Biology Society, vol. 12, No. 5, pp. 2051-2053, 1990.

Yamamoto et al., "Optical measurement of dental cast profile and application to analysis of three-dimensional tooth movement in orthodontics," *Frontiers in Med. and Biol. Eng'g*, vol. 1, No. 2 (1988), pp. 119-130.

Bartels, et al., "An Introduction to Splines for Use in Computer Graphics and Geometric Modeling," Morgan Kaufmann Publishers, 1987, pp. 422-425.

Blu, et al., "Linear interpolation revitilzed", *IEEE Transactions on Image Processing*, May 2004, 13(5), pp. 710-719.

Bourke, "Coordinate System Transformation," (Jun. 1996), p. 1, retrieved from the Internet Nov. 5, 2004, URL <http://astronomy.swin.edu.au/-pbourke/projection/coords>.

Carnaghan, "An Alternative to Holograms for the Portrayal of Human Teeth" 4th Int'l. Conf. on Holographic Systems, Components and Applications, Sep. 15, 1993, pp. 228-231.

English translation of Japanese Laid-Open Publication No. 63-11148 to inventor T. Ozukuri (Laid-Open on Jan. 18, 1998) pp. 1-7.

Fütterling et al., "Automated Fininte Element Modeling of a Human Mandible with Dental Implants," *WSCG '98 -Conference Program*, retrieved from the Internet: <http://wscg.zcu.cz/wscg98/papers98/Strasser_98.pdf>, 8 pages total.

Gottleib et al., "JCO Interviews Dr. James A. McNamura, Jr., on the Frankel Appliance: Part 2: Clinical Management," *Journal of Clinical Orthodonitics*, vol. 16, No. 6, (Jun. 1982) pp. 390-407.

Hikage, "Integrated Orthodontic Management System for Virtual Three-Dimensional Computer Graphic Simulation and Optical Video Image Database for Diagnosis and Treatment Planning", *Journal of Japan Orthodontic Society*, Feb. 1987, English translation, pp. 1-38, Japanese version, 46(2), pp. 248-269 (60 pages total).

Hojjatie et al., "Three-Dimensional Finite Element Analysis of Glass-Ceramic Dental Crowns," *J Biomech.* (1990) vol. 23, No. 11, pp. 1157-1166.

Kochanek, "Interpolating Splines with Local Tension, Continuity and Bias Control", *Computer Graphics*, Jul. 1984, 18(3), pp. 33-41.

Manetti et al., "Computer-aided Cefalometry and New Mechanics In Orthodontics" (Article Summary in English, article in German), *Fortschr. Kieferorthop.* 44, 370-376 (Nr. 5), 1983.

McCann, "Inside the ADA," *Journal Of The American Dental Assoc*, vol. 118 (Mar. 1989) pp. 286-294.

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Profit et al, *Contemporary Orthodontics* (Second Ed.) Chapter 15, Mosby Inc., (Oct. 1992), pp. 470-533.

Rekow et al., "CAD/CAM for Dental Restorations—Some of the Curious Challenges," *IEEE Transactions on Biomedical Engineering*, (Apr. 1991) vol. 38, No. 4, pp. 344-345.

Rekow et al., "Comparison of Three Data Acquisition Techniques for 3-D Tooth Surface Mapping," *Annual International Conference of the IEEE Engineering in Medicine and Biology Society*, (1991) vol. 13, No. 1, pp. 344-345.

Sinclair, "The Readers' Corner," *Journal of Clinical Orthodontics*, vol. 26, No. 6, (Jun. 1992), pp. 369-372.

Sturman, "Interactive Keyframe Animation of 3-D Articulated Models", *Proceedings Graphics Interface '84*, May-Jun. 1984, pp. 35-40.

Traux L., "Traux Clasp-Less™ Applicance System" *Funct. Orthod.*, 9(5):22-29 (Sep.-Oct. 1992).

Tru-Tain Orthodontic & Dental Supplies, Product Brochure, Rochester, Minnesota 55902, 16 pages total.

Verstreken et al., "An Image-Guided Planning System for Endosseous Oral Implants," *IEEE Transactions on Medical Imaging*, Oct. 1998, vol. 17, Issue 5, pp. 42-852.

Yamany et al., "A System for Human Jaw Modeling Using Intra-Oral Images," *Proc. of the 20th Annual Conf. of the IEE Eng'g in Medicine and Biology Society*, Nov. 1, 1998, vol. 2, pp. 563-566.

Yoshii, "Research on a New Orthodontic Appliance: The Dynamic Positioner (D.P.)-I. The D.P. Concept and Implementation of Transparent Silicone Resin (Orthocon)," *Nippon Dental Review*, vol. 452, Jun. 1980, pp. 61-74.

Yoshii, "Research on A New Orthodontic Appliance: The Dynamic Positioner (D.P.)-II. The D.P. Manufacturing Procedure and Clincal Applications," *Nippon Dental Review*, vol. 454, Aug. 1980, pp. 107-130.

Yoshii, "Research on a New Orthodontic Applicance: The Dynamic Positioner (D.P.)-III. The General Concept of the D.P. Method and Its Therapeutic Effect, Part 1, Dental and Functional Reversed Occulusion Case Reports," *Nippon Dental Review*, vol. 457, Nov. 1980, pp. 146-164.

Yoshii, "Research on a New Orthodontic Appliance: The Dynamic Positioner (D.P.)-III. The General Concept of the D.P. Method and Its Therapeutic Effect, Part 2. Skeletal reversed Occlusion Case Reports," *Nippon Dental Review*, vol. 458, Dec. 1980, pp. 112-129.

* cited by examiner

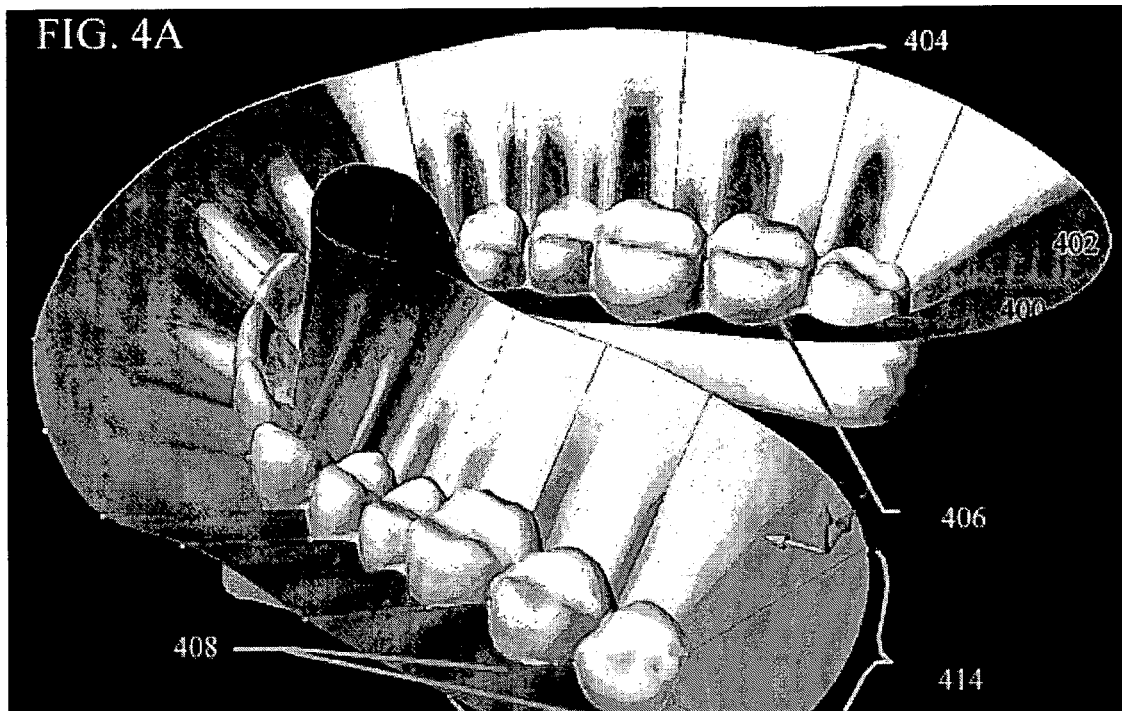
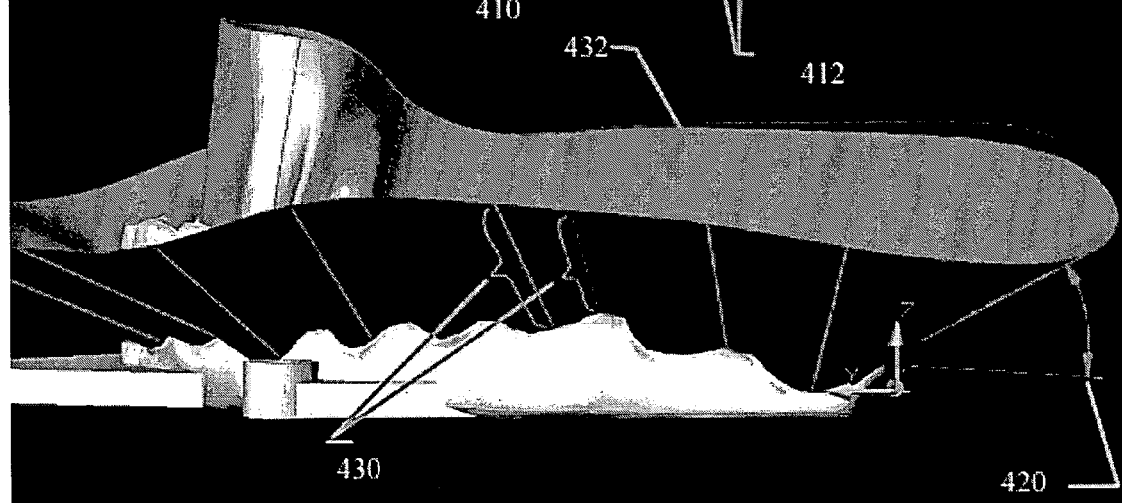

SYSTEMS AND METHODS FOR MASS CUSTOMIZATION

BACKGROUND

This invention relates to systems and methods for mass customization.

Mass customization is the application of mass production techniques to the production of parts that are different from each other and produced in rapid sequence. Mass-producing items that are generically similar to each other using production equipment that is rapidly modifiable or reprogrammable allows differences between these items. Typical limitations on the variability of product are inherent in the design of the manufacturing equipment; as an example, shoe-making machinery would not likely produce cars. Within limits, shoe-making machinery (for example) might produce different sizes, widths and even styles of shoes; this is possible with computer-controlled, automatic machinery. Such mass customization uses computer aided manufacturing (CAM) data that specifies process operations for each unique part.

Mass customization is especially suited for producing items that are based on, or made to work with organic forms. Organic, or natural shapes include plant and animal forms. Each of these forms is often a variation on a theme, either as a species or as an anatomical part. Typically moderate variations, in each organic category, are manageable by the adaptability of mass customization in making products to fit these forms. Examples of such products include apparel, surgical implants and prosthetic devices. The basic form of any of these products is common enough to be produced parametrically. Specific data, for each item produced, is entered into a table or template. The template represents the generic description, and the data entered into the template represents the specific description of the product.

Material removal or modification machinery is often controlled by a CAM program that requires specific information to define the geometry of the affected operation, the tool orientation, and the part being modified. Certain CAM programs automatically determine the entire machine operation mostly based on the desired final shape or condition of the part. Complex shapes, such as organic forms, generate very large descriptions of geometry in computerized formats, so CAM calculations are commensurately extensive for these shapes. These CAM calculations use surface geometry for tool orientation because material removal and modification are dependent on orientation of the tool axis in reference to the local surface. Also, surface transitions between convex and concave forms cause undulation of the tool and its motion system, when current CAM control is used. This complex mechanism motion is subject to accelerations that are limited by motor capacity and system stiffness, resulting in forces that cause wear; so accelerations are kept to moderate levels. Regulation of accelerations limits the average mechanism speed, an undesirable effect for rapid process execution. This process can be optimized by eliminating unnecessary accelerations by streamlining the path of mechanism motion.

CAM data flow and calculation speed are limited by file size, and tool progression speed is limited by undulation; so this whole process is very dependent on geometric complexity. CAM controlled machines operate at sub-optimal speed when they use organic surface geometry as a reference. For example, conventional CAM systems use surface data to define a toolpath, therefore, tool orientation is based on surface normals. Conventionally, the tool orientation will change radically to accommodate undulations that are prevalent in complex (organic) geometry, and this will require the tool head to move forward and backward along the toolpath, and generally to change direction erratically. This erratic motion is wasted motion, and it requires substantial positive & negative accelerations of the tool head.

SUMMARY

In one aspect, a method facilitates mass customization of an object having an ideal model surface by generating a template representing data common to the object; generating specific data to customize the object in conjunction with the template; and fabricating a customized version of the object.

Implementations of the above aspect may include one or more of the following. The method includes generating a tool-path to customize the object. The target path may be represented as a spline. The method includes creating an idealized tool-path from the ideal model surface. A mathematically smooth 3D spline using the idealized toolpath can be generated. The method includes generating surface normals from the ideal model surface at points distributed around the idealized toolpath. Each surface normal can be displaced from its end to the nearest point on the smooth 3D spline. A spline can be created for connecting each unattached end of each surface normal. The ends are attached sequentially in a loop. A source spline can be used to define motion of the tool head by defining tool orientation vectors, and subsequent motion of a tool head. The source spline can be adjusted, such as by moderate elevation or lowering of the angle of the surface normal.

In another aspect, a method fabricates an object having an ideal model surface by receiving a digital representation of a target path; generating a mathematically smoothed version of the target path; applying the smoothed target path as a base to generate a secondary target path; and generating a streamlined tool-path to fabricate the object.

In yet another aspect, a method optimizes data flow, CAM calculation and mechanism motion by applying a statistical concept to the creation of toolpaths.

In another aspect, a template is used to generate a toolpath for laser cutting the margins of an object.

Advantages of the invention may include one or more of the following. The techniques support rapid mass customization with rapid execution of data streaming, CAM calculations, and process device actions. The amount of data required by CAM for processing instructions to control material removal or modification machinery is reduced. The technique is advantageous for rapid workpiece changing situations that use dissimilar, but generically related shapes for workpieces and where the depth of action is not critical. Appropriate processes include cutting, surface conditioning, trimming and welding with laser, plasma torch, and water jet as well as other projection-to-surface style devices.

In addition to reducing the processing and handling of data, the techniques also streamline the motion for the trim devices. These advantages can be attributed in part to the source spline. The source spline effectively reduces data requirements by extracting common data from the calculation process, and adding it back in as a template by incorporating it into the algorithm. Motion streamlining is achieved by eliminating undulated movement of the tool head along the source spline.

BRIEF DESCRIPTION OF THE DRAWINGS

FIGS. 4A–4B are exemplary illustrations of trimming operations using splines.

DESCRIPTION

Figure 1:
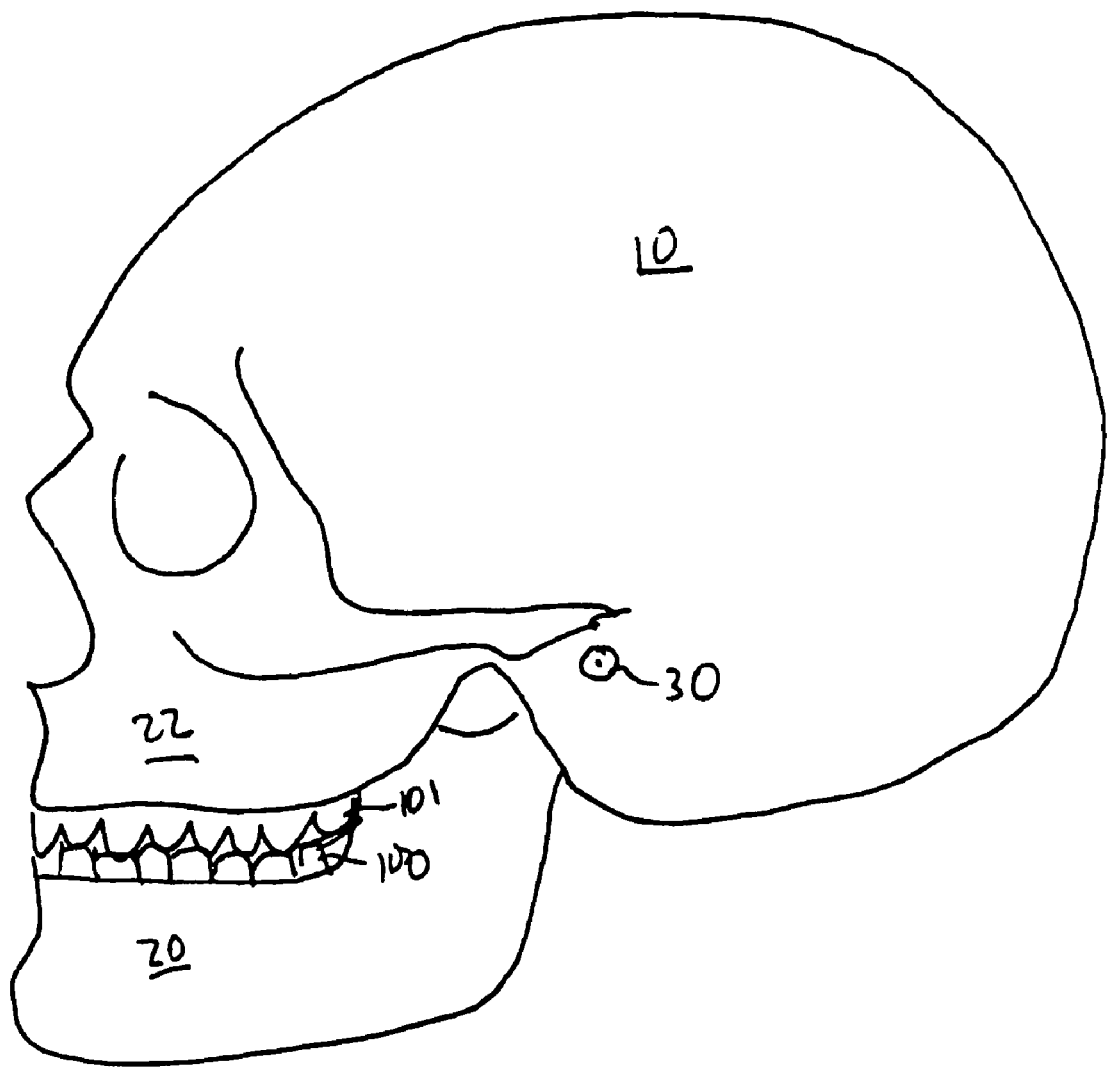
FIG. 1 is an elevational diagram showing the anatomical relationship of the jaws of a patient.

FIG. 1 shows a skull 10 with an upper jaw bone 22 and a lower jaw bone 20. The lower jaw bone 20 hinges at a joint 30 to the skull 10. The joint 30 is called a temporal mandibular joint (TMJ). The upper jaw bone 22 is associated with an upper jaw 101, while the lower jaw bone 20 is associated with a lower jaw 100. A computer model of the jaws 100 and 101 is generated in accordance with the process of FIG. 3, and a computer simulation can model interactions among the teeth on the jaws 100 and 101. The computer simulation allows the system to focus on motions involving contacts between teeth mounted on the jaws. The computer simulation allows the system to render realistic jaw movements that are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
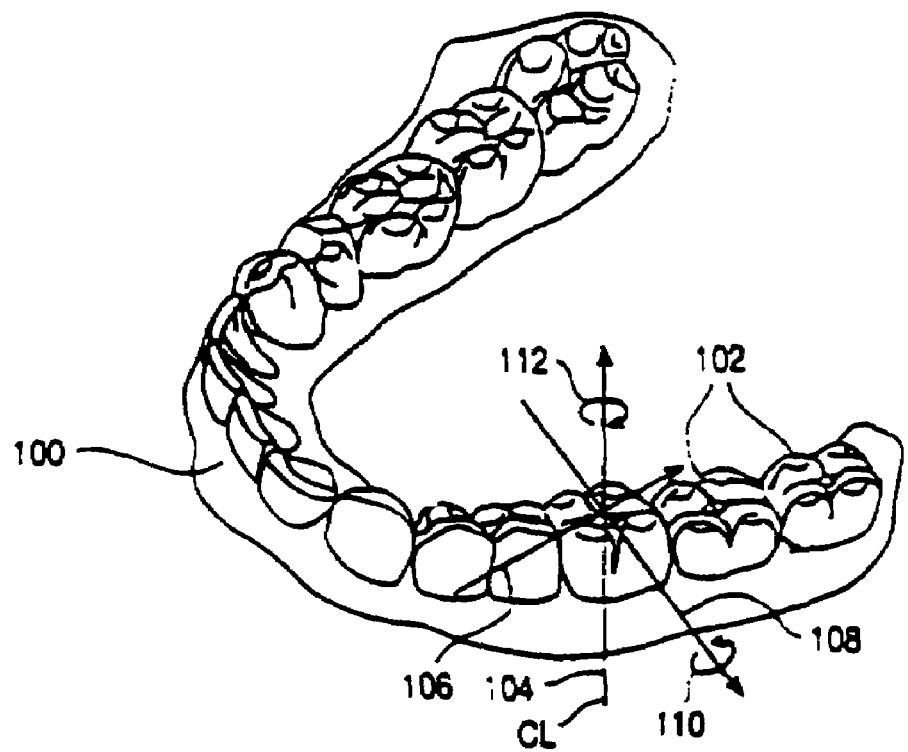
FIG. 2A illustrates in more detail the patient's lower jaw and provides a general indication of how teeth may be moved by the methods and apparatus of the present invention.

Referring now to FIG. 2A, the computer model of the lower jaw 100 includes a plurality of teeth 102, for example. At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 114. Thus, all possible free-form motions of the tooth can be performed.

Figure 2B:
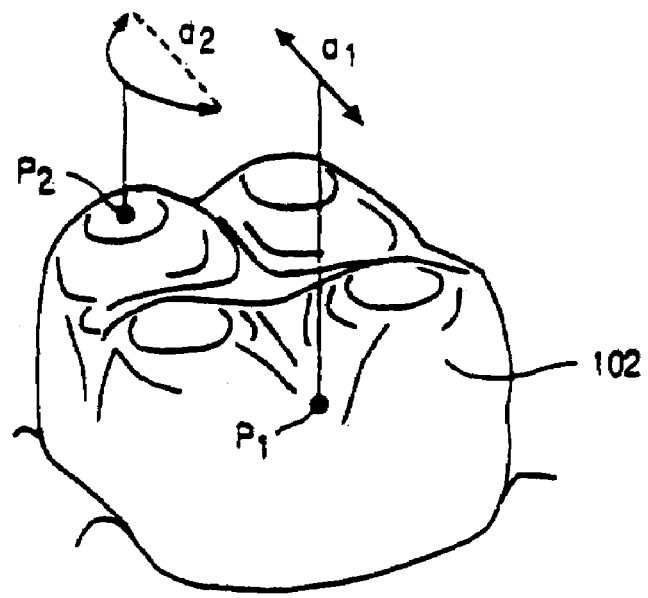
FIG. 2B illustrates a single tooth from FIG. 2A and defines how tooth movement distances are determined.

FIG. 2B shows how the magnitude of any tooth movement may be defined in terms of a maximum linear translation of any point P on a tooth 102. Each point P1 will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point P1 may in fact undergo a true side-to-side translation as indicated by arrow d1, while a second arbitrary point P2 may travel along an arcuate path, resulting in a final translation d2. Many aspects of the present invention are defined in terms of the maximum permissible movement of a point P1 induced on any particular tooth. Such maximum tooth movement, in turn, is defined as the maximum linear translation of that point P1 on the tooth that undergoes the maximum movement for that tooth in any treatment step.

Figure 2C:
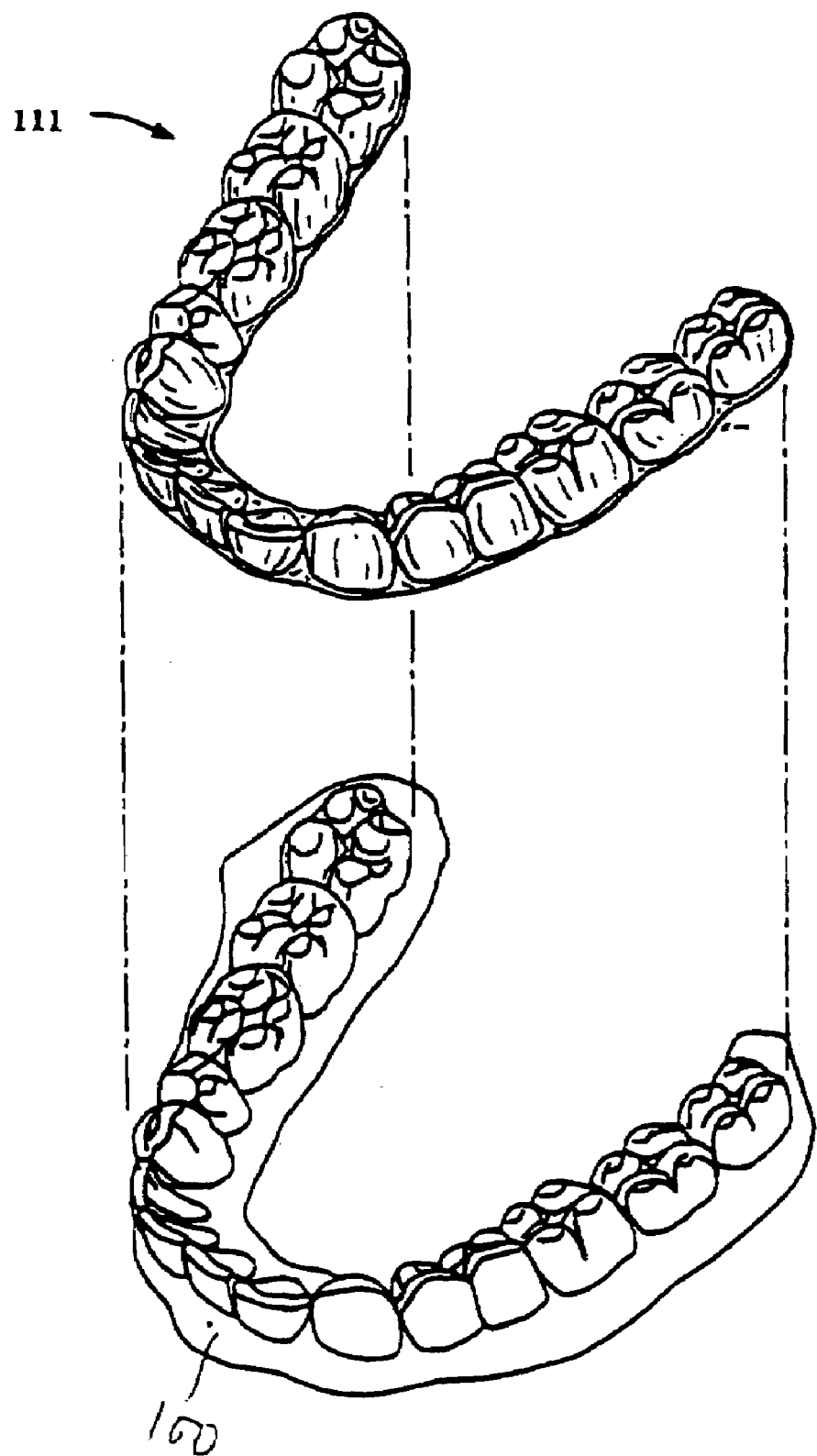
FIG. 2C illustrates the jaw of FIG. 2A together with an incremental position adjustment appliance.

FIG. 2C shows one adjustment appliance 111 which can be worn by the patient in order to achieve an incremental repositioning of individual teeth in the jaw as described generally above. The appliance is a polymeric shell having a teeth-receiving cavity, as described in U.S. Pat. No. 5,975,893, entitled "Method and system for incrementally moving teeth," the full disclosures of which are incorporated by reference.

As set forth in the prior applications, each polymeric shell may be configured so that its tooth-receiving cavity has a geometry corresponding to an intermediate or final tooth arrangement intended for the appliance. The patient's teeth are repositioned from their initial tooth arrangement to a final tooth arrangement by placing a series of incremental position adjustment appliances over the patient's teeth. The adjustment appliances are generated at the beginning of the treatment, and the patient wears each appliance until the pressure of each appliance on the teeth can no longer be felt. At that point, the patient replaces the current adjustment appliance with the next adjustment appliance in the series until no more appliances remain. Conveniently, the appliances are generally not affixed to the teeth and the patient may place and replace the appliances at any time during the procedure.

The polymeric shell 111 can fit over all teeth present in the upper or lower jaw. Often, only certain one(s) of the teeth will be repositioned while others of the teeth will provide a base or an anchor region for holding the appliance 111 in place as the appliance 111 applies a resilient repositioning force against the tooth or teeth to be repositioned. In complex cases, however, multiple teeth may be repositioned at some point during the treatment. In such cases, the moved teeth can also serve as a base or anchor region for holding the repositioning appliance.

The polymeric appliance 111 of FIG. 2C may be formed from a thin sheet of a suitable elastomeric polymer, such as Tru-Tain 0.03 in, thermal forming dental material, available from Tru-Tain Plastics, Rochester, Minn. Usually, no wires or other means will be provided for holding the appliance in place over the teeth. In some cases, however, it will be desirable or necessary to provide individual anchors on teeth with corresponding receptacles or apertures in the appliance 100 so that the appliance can apply an upward force on the tooth that would not be possible in the absence of such an anchor.

Figure 3:
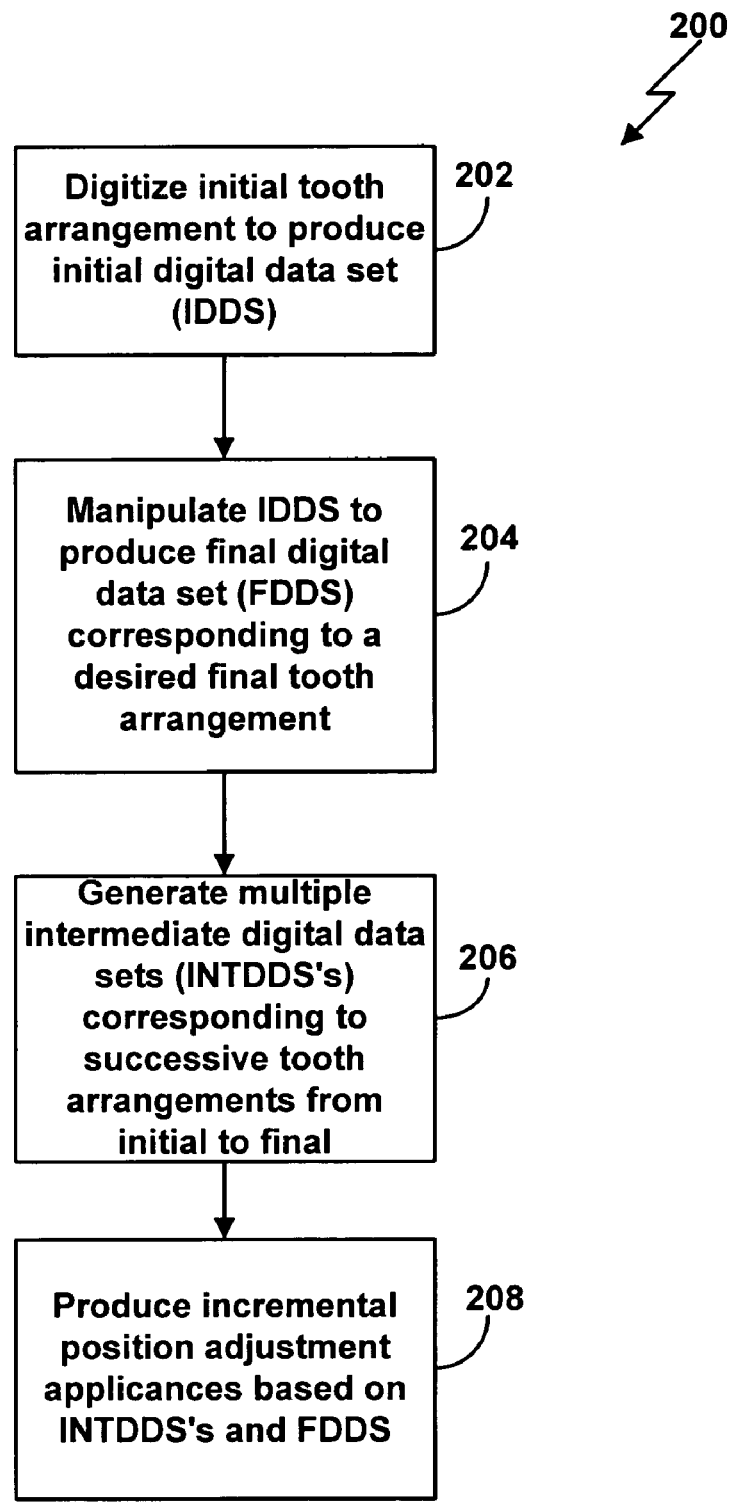
FIG. 3 is a block diagram illustrating a process for producing incremental position adjustment appliances.

FIG. 3 shows a process 200 for producing the incremental position adjustment appliances for subsequent use by a patient to reposition the patient's teeth. The flow chart of FIG. 3 is for purpose of explanation and does not necessarily reflect all possible paths of control flow in the execution of the client program.

As a first step, an initial digital data set representing an initial tooth arrangement is obtained (step 202). The initial data set may be obtained in a variety of ways. For example, the patient's teeth may be scanned or imaged using X-rays, three dimensional X-rays, computer-aided tomographic images or data sets, or magnetic resonance images, among others. The teeth data may be generated by a destructive scanner, as described in the incorporated-by-reference U.S. application Ser. No. 09/169,034, filed Oct. 8, 1998. The initial data set is then manipulated using a computer having a suitable graphical user interface (GUI) and software appropriate for viewing and modifying the images. More specific aspects of this process will be described in detail below. Individual tooth and other components may be segmented or isolated in the model to permit their individual repositioning or removal from the digital model.

After segmenting or isolating the components, the teeth are moved based on rules and algorithms programmed into the computer. In this step, each stage of tooth movement is determined by an attraction model between selected points on adjacent teeth. This step is iterated until an acceptable result is achieved (step 206). In one embodiment, the system stops the movement when the relative positions of the teeth satisfy a predetermined target.

In step 206, positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement, which is customized to the patient's teeth, as discussed below. After applying the ideal model to the computer representation, the position of the teeth can be optimized to fit the ideal model. The ideal model may be specified by one or more arch forms, or may be specified using various features associated with the teeth.

Once the teeth arrangements are determined, a series of appliances that move the teeth in a specified sequence are generated (step 208). For example, the teeth models may be rotated until their roots are in the proper vertical position. Next, the teeth models may be rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together can be visualized using a collision detection process to highlight the contacting points of the teeth.

During manufacturing, the appliances need to be cut or trimmed. The processes described below generate toolpaths from geometric input to define automated motion of a computer-controlled device to trim objects such as appliances. The application of this technique is more appropriate for complex, three-dimensional solid or surface geometry, both in reference to the toolpath and to the basic shape used to create the toolpath (i.e., the workpiece). However, the techniques can be applied to two-dimensional geometry as well.

FIGS. 4A, 4B, 5 and 6 show embodiments applied to defined automated motion of a computer-controlled device to generate a physical model based on a dental arch. FIG. 4A shows a ribbon 400 surrounding an object 402. In this embodiment, the object 402 is a model of a dental arch of teeth. The ribbon 400 represents a toolpath for a trimming operation, and the teeth model represents complex geometry that the toolpath is specifically generated for. The top edge of this ribbon 400 is a template or source spline 404 that is common to all toolpaths, whereas the bottom edge is the target spline, unique to each file that is downloaded to the CAM system. The template is a parametric table or form that can be customized to a specific object.

Information required to control the trim motion is contained in one or more ribbon components, including the source spline or template 404, a target spline 406, synchronization points 410 on the source spline or template 404, and target points 408 on the target spline 406. The ribbon surface and synchronization lines may be inferred from spline data and synchronization data.

The source spline 404 works in conjunction with the target spline 406. A physical or geometric relationship exists between the source spline 404 and the target spline 406 that defines a surface swept between the source spline 404 and the target spline 406. The geometric relationship is expressed as the tool path and represents the vectors for the tool. Exemplary vectors include the perimeter of a rotary tool such as a milling cutter or the center line of a beam of light from a laser or a beam of fluid from a water jet cutter.

During processing, synchronization lines 412 are projected from the synchronization point 410 to target point 408. The synchronization point 410 can be pre-established in position on the source spline or template 404. The target point 408 that correlates with the synchronization point 410 should be positioned on the target spline 406. In one embodiment, an orthogonal or plan view of FIG. 4A can be used to generate orientations for synchronization lines 412 that appear as surface normals to the target spline 406. The direction for each projection is from the source spline (404) to the target spline (406) and represents the equivalent of surface normals to the smoothed target spline 452 (mathematically smoothed 3D spline). The projection is done such that the synchronization lines 412 are substantially orthogonal to the mathematically smooth spline 452. The length of the surface normals is adjustable. Long normals tend to resemble the average more than short normals since angular changes from specific target splines change more radically with angular changes for short normals. Short normals tend to provide high resolution at the expense of more data having to flow through the CAM system. Alternatively, long normals would provide faster motion at the expense of precision and resolution because the angular changes have to be accurately controlled.

The template takes common information required for the CAM process as a standard for all cases in mass customization. By applying a relatively simple set of data that represents the differences between all of the different parts, the template 404 can be adapted for each object 402 to customize the output. The information embodied in the template may be streamlined. One optimization removes CAM calculations that are based on specific solid geometry from the toolpath generation process. In such an optimization, surface undulations are ignored. The optimization of tool head velocity can be achieved by minimizing the number, magnitudes and durations of accelerations because these parameters have deleterious effect on average velocity. The template minimizes these degradations of toolpath motions by ignoring their source.

In one embodiment, one or more generic files are categorized so that similar shapes are defined within parametric limits such as size or shape within a superset; for example, small dental arches are distinguished from large arches. In one implementation, code can be provided in the file for calling the template 404. In another embodiment, a hierarchical format is used to enhance the adaptability of CAM to fit a wide range of shapes that a specific process would be applied to; for example, modification of bone implants for different types of bones. The source spline shape and other parametric data can be grouped under headings or subheadings.

FIG. 4B is another view of FIG. 4A. FIG. 4B shows the object 402 resting on a support 430. FIG. 4B also shows a smooth path 432 for the motion of the system of the laser 404. In the exemplary embodiment of FIG. 4B, trim vectors 420 are approximately forty degrees relative to object surface normals. The object 402 bears a generalized relationship to the surface normals so that the angle is constant in this example. The surface normals of FIG. 4B follow a predetermined formula that is based on an idealized model of the object 402.

The motion system of FIGS. 4A and 4B follows the tool path has a motion that is generally smooth and constantly leading. As the motion system follows the source spline 404 or an equivalent of the source spline 404, its motion is smooth. Further, any vectors that relate to a position at any moment in time of the motion system at 404 as it moves forward also relates to a forward motion along the target spline (408). Thus, a correlated move generally exists in the forward direction between the motion system and the target object itself.

Figure 5:
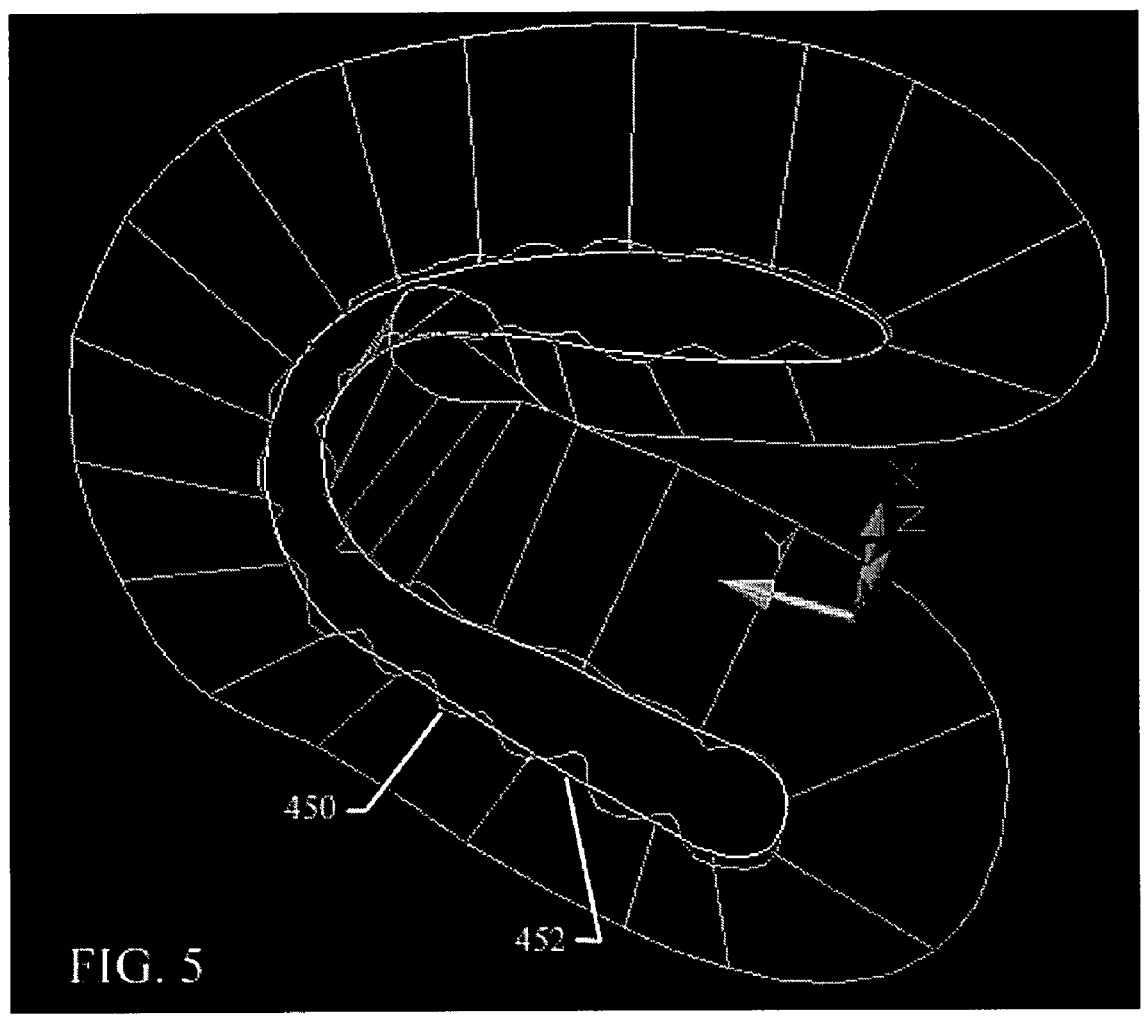
FIG. 5 is an exemplary illustration of a smoothed 3D spline and an ideal toolpath.

FIG. 5 shows in more detail the relationship between an idealized tool-path 450 and a mathematically smoothed spline 452. A transition or translation process mathematically converts the idealized tool path 450 into a spline 452 that is a mathematically smoothed 3D spline. The mathematically smoothed spline generally follows a monotonic curvature in all three dimensions. The mathematically smoothed 3D spline is used in an intermediate step that generates a set of synchronization lines which are all the same length and which have been adjusted specifically so that the other ends of the synchronization line are connectable together by another 3D spline that becomes a source spline. The mathematically smoothed spline is provided to a CNC controller that generates a smooth tool path and drives the tool head motion itself. An end-effector of the tool can articulate around the target object using a numerically controlled (NC) axis or rotary axis that changes the vector from any given points along the source spline 404.

In FIG. 5, synchronization lines 412 that descend from the top spline to the bottom spline are representative of the direction (vector) of the trim beam or tool axis at different positions around the path. The CAM interpolates the toolpath between synchronization lines. Due to the interpolation, the resulting motion of the source device (laser motion devices) is smooth and progressive without sharp turns or reversals. In embodiments where the source device is a laser or projected beam device where effective focus occurs with substantial focal depth, the source device does not need to track the target along the axis of the trim beam, even though the target spline articulates in this beam-axis direction.

Figure 6:
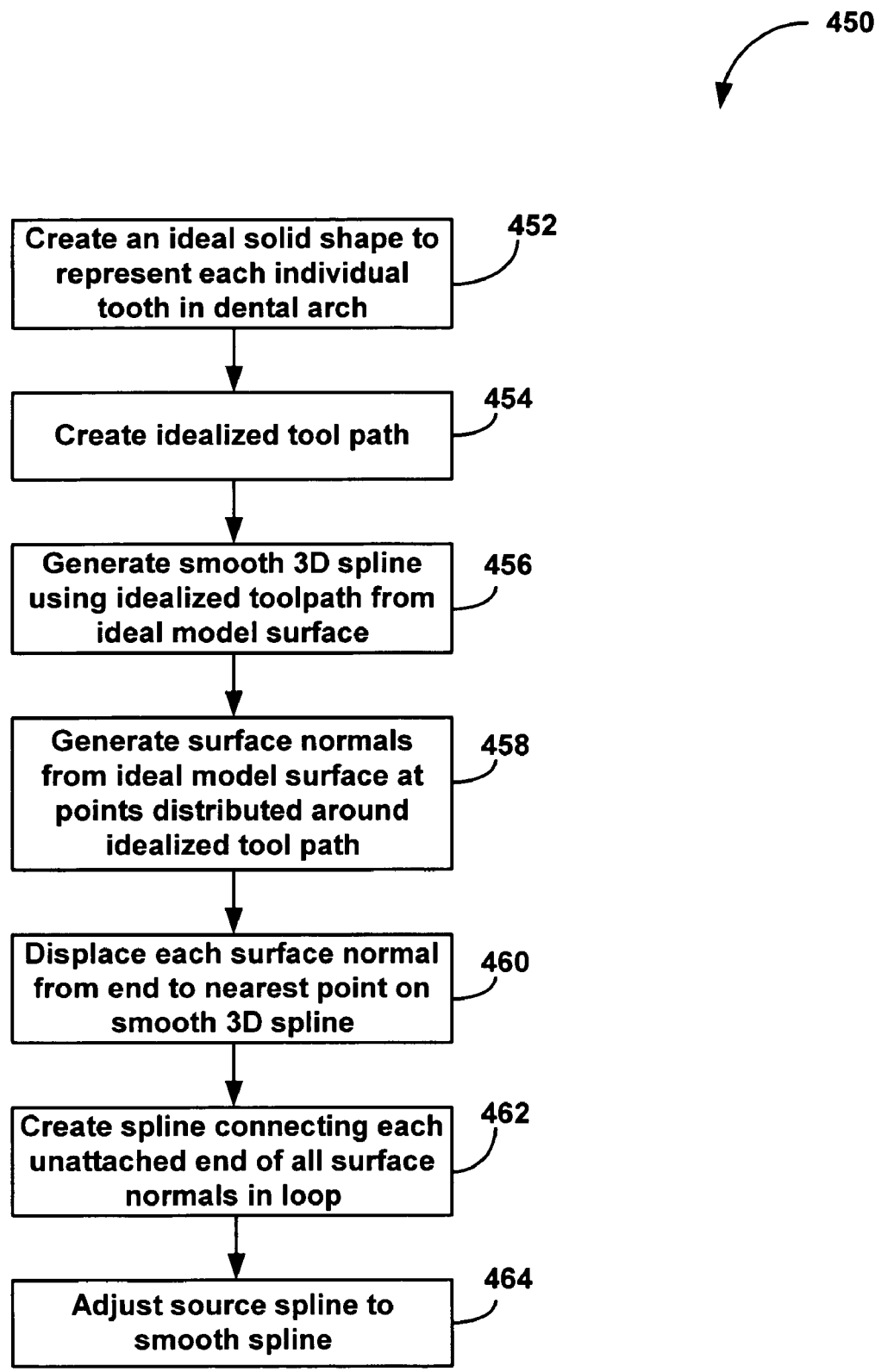
FIG. 6 is a flow chart illustrating a process for smoothing splines.
Figure 7:
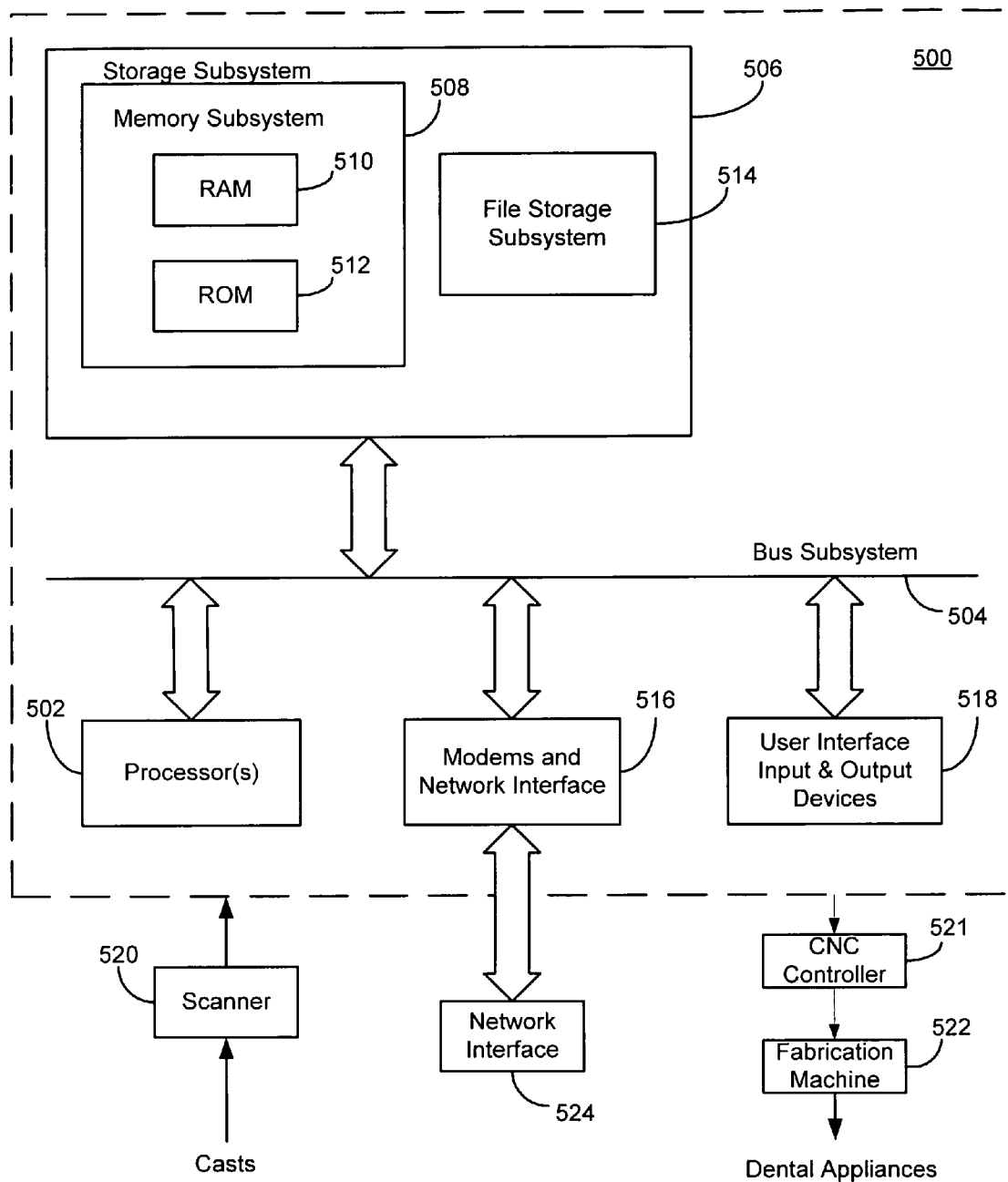
FIG. 7 is a block diagram illustrating a system for generating appliances in accordance with the present invention.

FIG. 6 shows a process 450 to generate a smoothed spline for trimming an object. The smoothing of a spline such as a source spline first requires the creation of an ideal model surface or solid shape (step 452). In an embodiment, the ideal model surface or shape can be a 3D statistical mean. In another embodiment, the ideal surface or solid shape may represent all individual models, a dental arch in this example. After this ideal model is created, the process 450 creates an idealized toolpath (step 454). The idealized toolpath can consist of a 3D spline that is anchored to the surface of the model. This toolpath may follow a surface feature such as the gum line of this dental model, or follow a design feature. Next, the process 450 generates a (mathematically) smooth 3D spline using the idealized toolpath (equivalent to the target spline) from the ideal model surface (step 456). The process 450 then generates surface normals from the ideal model surface at points distributed around the idealized toolpath (step 458). These surface normals should be the same length, preferably matching the distance from the closest rotary axis of the motion system. Elevate or lower these normals by a consistent angle, if required; the example shows 40-degree elevation. The process 450 then displaces each surface normal from its end to the nearest point on the smooth 3D spline (step 460). Step 460 displaces the surface normals from the idealized spline which is rather curvy into the mathematically smoothed 3D spline to create a set of surface normals or synchronization lines that have an angular relationship to the surface normals. The endpoints are connectable with the smooth spline that then in turn creates the source spline.

A spline is created that connects each unattached end of all the surface normals sequentially in a loop (step 462). This spline will be the source spline that will define motion of the tool head by defining tool orientation vectors, and subsequent motion of the tool head itself. If this source spline is not smooth, it may be adjusted (step 464). In one embodiment, the adjustment includes a moderate elevation or lowering of the angle of each surface normal using the target spline intersection as a pivot axis, and alteration of the source spline. This adjustment will beneficially affect streamlining of the tool head motion and action of the tool on the surface of the workpiece.

The smoothed spline generated using the process 450 is then used to cut or trim the object. The source spline data is loaded as part of a template of a computer aided manufacturing (CAM) system. This makes the CAM system capable of accepting specific target spline data as a complement that fulfills most data requirements needed to generate a specific toolpath. The template can include data requirements, and part orientation information for fixturing the workpiece must be included in the template to assure the correlation of geometry between the device toolpath and the workpiece during operation. Part orientation is established with a three-axis Cartesian datum that is common between the ideal model and all specific models. Additional common data incorporated in the template may include other process parameters such as motion velocities, effecter power (flow rate, flow velocity, focus, etc.), temperature, and pulse rate. The template can also include algorithms for adjustment of process parameters that are triggered by special geometric conditions of the target spline or by special notation attached to the target spline file.

The target spline data is also loaded into the CAM system to generate coded instructions for the motion controller. This data describes the 3D spline and its reference datum. Additional information may be added for assisting control through the CAM program in a manner that distinguishes the specific file model from the ideal model, including part querying and verification of a match through machine vision or other similar means.

FIG. 6 is a simplified block diagram of a data processing system 500 for handling CAM operations. Data processing system 500 typically includes at least one processor 502 that communicates with a number of peripheral devices over bus subsystem 504. These peripheral devices typically include a storage subsystem 506 (volatile memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe. The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used. User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514. Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system). File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web. In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations. Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524. Fabrication machine 522 fabricates dental appliances based on intermediate and final data set information received from data processing system 500. In a distributed environment, fabrication machine 522 may be located at a remote location and receive data set information from data processing system 500 over network interface 524.

The computer system 500 receives specific geometric data or in this case specific 3D spline target data and produces an output that is understandable by a controller 521. The controller 521 interprets computer code from the computer 500 into instructions for electromechanical actuators such as motors, for example. The instructions specify acceleration ramps, velocities, changes in velocities, pulse rate, the relationship between certain motions or timing sequence and the different axes. In one embodiment with five axis, five different motors, three motors describing X, Y and Z motion and two motors describing rotary motion about two of the axes.

Various alternatives, modifications, and equivalents may be used in lieu of the above components. The commercial manifestation of the concept of templates could take different forms. One form might be as an algorithm or subprogram within CAM. Another form could be as a separate program that would work with a variety of CAM programs. A third option would be as proprietary software, developed and used internally within a company. It should be noted that this invention, if patented, would have no practical enforceability outside the commercial forms. Development of software within a company for application within that company cannot be controlled outside that company; this fact makes strong development of a commercial format attractive.

While the invention has been shown and described with reference to an embodiment thereof, those skilled in the art will understand that the above and other changes in form and detail may be made without departing from the spirit and scope of the following claims.

What is claimed is:

1. A method for facilitating mass customization of an object, the object comprising a dental appliance, the method comprising:
   generating a template representing data common to a plurality of different dental appliances, the template comprising a source spline;
   generating specific data to customize an appliance in conjunction with the template, the specific data comprising a target spline; wherein the source spline and the target spline define at least one tool path; and
   directing at least one tool along the at least one tool path to fabricate a customized version of the appliance.

2. The method of claim 1, wherein the tool path is represented as a spline.

3. The method of claim 1, wherein the object has an ideal model surface, wherein generating the specific data comprises creating an idealized tool path from the ideal model surface.

4. The method of claim 3, further comprising generating a mathematically smooth 3D spline using the idealized tool path.

5. The method of claim 4, further comprising generating surface normals from the ideal model surface at points distributed around the idealized tool path.

6. The method of claim 5, further comprising displacing each surface normal from its end to a nearest point on the smooth 3D spline.

7. The method of claim 6, further comprising creating a spline connecting each unattached end of each surface normal.

8. The method of claim 7, wherein the ends are attached sequentially in a loop.

9. The method of claim 1, wherein directing the tool comprises using a source spline to define motion of the tool by defining tool orientation vectors.

10. The method of claim 9, further comprising adjusting the source spline.

11. The method of claim 10, wherein the source spline is adjusted by moderately elevating or lowering an angle of a surface normal.

12. A method for fabricating a customized object, the method comprising:
- receiving a digital representation of a target path;
- generating a mathematically smoothed version of the target path;
- applying the smoothed target path to generate a secondary target path;
- generating a streamlined tool path, based on the secondary target path; and
- directing a tool along the tool path to fabricate the customized object, the customized object comprising a customized dental appliance having cavities shaped to receive and resiliently reposition a patient's teeth.

13. The method of claim 12, wherein the target path is represented as a spline.

14. The method of claim 12, wherein the object has an ideal model surface, further comprising creating an idealized tool path from the ideal model surface.

15. The method of claim 14, further comprising generating a mathematically smooth 3D spline using the idealized tool path.

16. The method of claim 15, further comprising generating surface normals from the ideal model surface at points distributed around the idealized tool path.

17. The method of claim 16, further comprising displacing each surface normal from its end to a nearest point on the smooth 3D spline.

18. The method of claim 17, further comprising creating a spline that connects each unattached end of each surface normal and wherein the ends are attached sequentially in a loop.

19. The method of claim 12, wherein directing the tool along the tool path comprises using a source spline to define motion of the tool by defining tool orientation vectors.

20. The method of claim 19, further comprising adjusting the source spline moderately elevating or lowering an angle of a surface normal.

21. A method for facilitating mass customization of an object, the object comprising an article of manufacture, the method comprising:
- generating a template representing data common to a plurality of different objects, the template comprising a source spline;
- extracting the common data from a calculation process used in object fabrication;
- generating specific data to customize the object in conjunction with the template, the specific data comprising a target spline; wherein the source spline and the target spline define at least one tool path; and
- directing at least one tool along the at least one tool path to fabricate a customized version of the object.

22. The method claim 21, wherein the calculation process is a CAM process.

23. The method claim 21, wherein the object is an in incremental tooth adjustment appliance.

24. The method of claim 1, wherein the dental appliance comprises cavities shaped to receive and resiliently reposition a patient's teeth.

25. The method of claim 21, wherein the article of manufacture comprises a dental appliance having cavities shaped to receive and resiliently reposition a patient's teeth.

* * * * *